(12) United States Patent
Globerman et al.

(10) Patent No.: US 6,287,336 B1
(45) Date of Patent: Sep. 11, 2001

(54) VARIABLE FLEXIBILITY STENT

(75) Inventors: Oren Globerman, Holon; Mordechay Beyar, Caeseria; Rafael Beyar, Haifa, all of (IL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/101,705

(22) PCT Filed: Nov. 7, 1997

(86) PCT No.: PCT/US97/20695

§ 371 Date: May 13, 1999

§ 102(e) Date: May 13, 1999

(87) PCT Pub. No.: WO98/22159

PCT Pub. Date: May 28, 1998

Related U.S. Application Data

(63) Continuation-in-part of application No. 08/942,648, filed on Oct. 2, 1997, now Pat. No. 6,090,127, which is a continuation of application No. 08/543,337, filed on Oct. 16, 1995, now Pat. No. 5,776,161

(60) Provisional application No. 60/029,936, filed on Nov. 7, 1996.

(51) Int. Cl.[7] .................................................. A61F 2/00

(52) U.S. Cl. ............................................. 623/1.3; 623/1.15

(58) Field of Search ..................................... 623/1.1, 1.15, 623/1.16, 1.3, 1.31

(56) References Cited

U.S. PATENT DOCUMENTS

| 4,776,337 | 10/1988 | Palmaz . |
| 4,816,028 | 3/1989 | Kapadia et al. . |

(List continued on next page.)

FOREIGN PATENT DOCUMENTS

| 0 800 801 A1 | 10/1997 | (EP) . |
| WO 97/21399 | 6/1997 | (WO) . |
| WO 97/25937 | 7/1997 | (WO) . |
| WO 97/32543 | 9/1997 | (WO) . |
| WO 98/18404 | 5/1998 | (WO) . |

* cited by examiner

Primary Examiner—Michael Milano
(74) Attorney, Agent, or Firm—Mueting, Raasch & Gebhardt, P.A.

(57) ABSTRACT

A stent (1) is provided for having variable flexibility and stiffness along its length. The stent (1) comprises portions (5, 7, 9, 11, 13, 15) of the stent having different bending and durability characteristics, and may be fabricated, using any of a variety of methods out of any of a variety of materials.

10 Claims, 3 Drawing Sheets

U.S. PATENT DOCUMENTS

| | | |
|---|---|---|
| 4,856,516 | 8/1989 | Hillstead . |
| 4,893,623 | 1/1990 | Rosenbluth . |
| 4,969,458 | 11/1990 | Wiktor . |
| 4,994,071 | 2/1991 | MacGregor . |
| 5,019,085 | 5/1991 | Hillstead . |
| 5,104,404 | 4/1992 | Wolff . |
| 5,116,365 | 5/1992 | Hillstead . |
| 5,135,536 | 8/1992 | Hillstead . |
| 5,178,618 | 1/1993 | Kandarpa . |
| 5,234,457 | 8/1993 | Andersen . |
| 5,282,824 | 2/1994 | Gianturco . |
| 5,293,879 | 3/1994 | Vonk et al. . |
| 5,314,472 | 5/1994 | Fontaine . |
| 5,342,387 * | 8/1994 | Summers . |
| 5,366,473 | 11/1994 | Winston et al. . |
| 5,383,892 | 1/1995 | Cardon et al. . |
| 5,389,106 | 2/1995 | Tower . |
| 5,421,955 | 6/1995 | Lau et al. . |
| 5,443,496 * | 8/1995 | Schwartz ................................ 623/1 |
| 5,449,373 * | 9/1995 | Pinchasik ................................ 623/1 |
| 5,507,767 | 4/1996 | Maeda et al. . |
| 5,514,154 | 5/1996 | Lau et al. . |
| 5,527,354 | 6/1996 | Fontaine et al. . |
| 5,540,712 | 7/1996 | Kleshinski et al. . |
| 5,540,713 | 7/1996 | Schnepp-Pesch et al. . |
| 5,549,662 | 8/1996 | Fordenbacher . |
| 5,549,663 | 8/1996 | Cottone, Jr. . |
| 5,554,181 | 9/1996 | Das . |
| 5,591,197 | 1/1997 | Orth et al. . |
| 5,591,198 | 1/1997 | Boyle et al. . |
| 5,607,442 | 3/1997 | Fischell et al. . |
| 5,607,445 | 3/1997 | Summers . |
| 5,613,981 | 3/1997 | Boyle et al. . |
| 5,630,829 | 5/1997 | Lauterjung . |
| 5,636,641 | 6/1997 | Fariabi . |
| 5,643,312 | 7/1997 | Fischell et al. . |
| 5,653,727 | 8/1997 | Wiktor . |
| 5,681,346 | 10/1997 | Orth et al. . |
| 5,697,971 | 12/1997 | Fischell et al. . |
| 5,725,572 | 3/1998 | Lam et al. . |
| 5,728,158 | 3/1998 | Lau et al. . |
| 5,733,303 | 3/1998 | Israel et al. . |
| 5,735,893 | 4/1998 | Lau et al. . |
| 5,741,327 | 4/1998 | Frantzen . |
| 5,749,919 * | 5/1998 | Blanc ................................ 623/1 |
| 5,755,776 | 5/1998 | Al-Saadon . |
| 5,759,192 | 6/1998 | Saunders . |
| 5,766,238 | 6/1998 | Lau et al. . |
| 5,776,161 | 7/1998 | Globerman . |
| 5,807,404 * | 9/1998 | Richter ................................ 623/1 |
| 5,855,600 * | 1/1999 | Alt ................................ 623/1 |

LOADING CONDITIONS       BENDING MOMENT GRAPHS

UNIFORM LOAD

MOMENT DIAGRAM
ALONG THE STENT

SINGLE LOAD

MOMENT DIAGRAM
ALONG THE STENT

TORQUE

MOMENT DIAGRAM
ALONG THE STENT

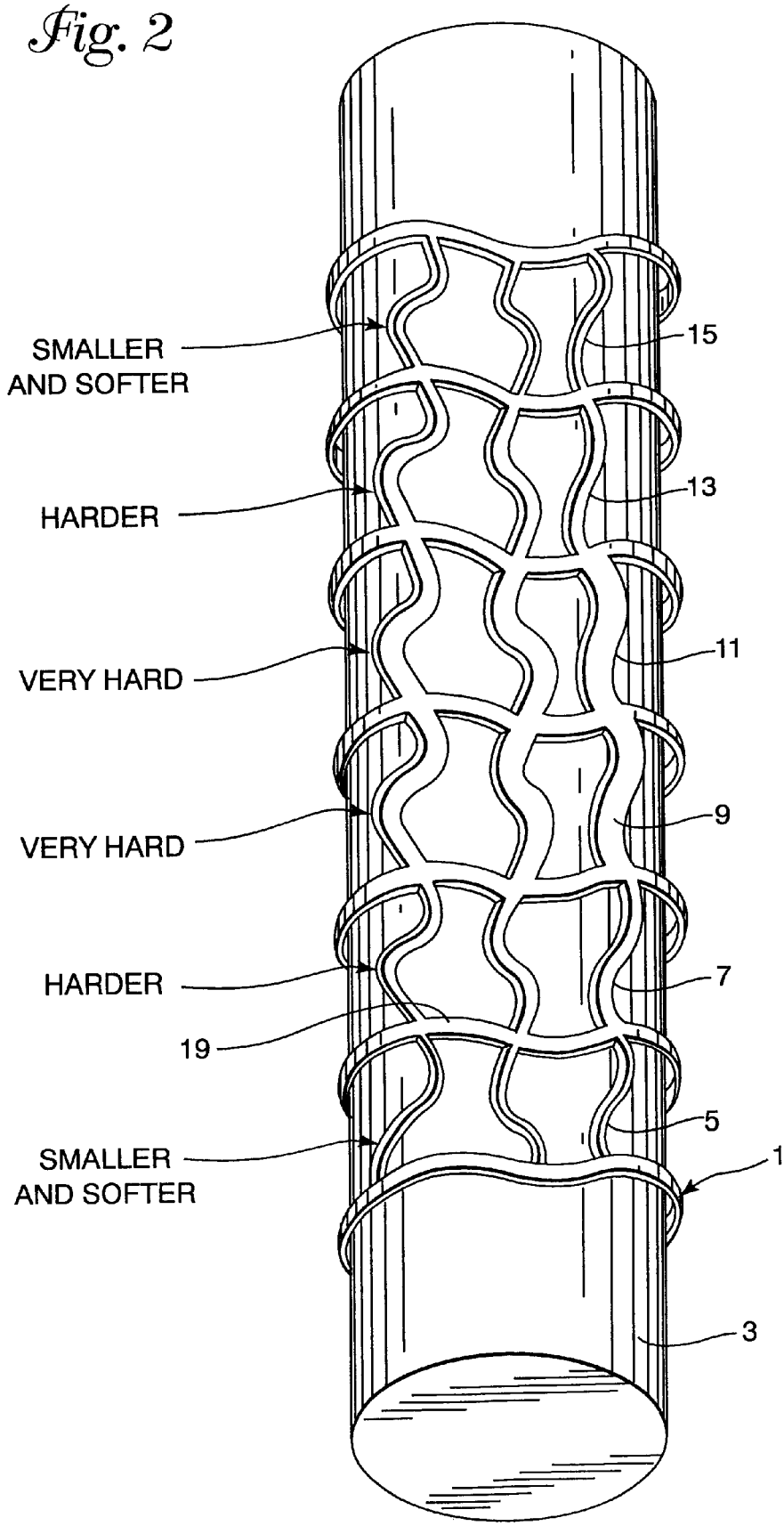

VARIABLE FLEXIBILITY STENT

This application is the National Stage of International Application No. PCT/US97/20695, filed Nov. 7, 1997, which claims the benefit of U.S. Provisional Application Ser. No. 60/029,936, filed Nov. 7, 1996; and is a continuation-in-part of U.S. patent application Ser. No. 08/942,648, filed Oct. 2, 1997 now U.S. Pat. No. 6,090,127; which is a continuation of U.S. patent application Ser. No. 08/543,337, filed Oct. 16, 1995, now U.S. Pat. No. 5,776,161.

FIELD OF THE INVENTION

This invention concerns a novel stent. More particularly, this invention concerns a stent having variable flexibility and stiffness.

BACKGROUND OF THE INVENTION

A common characteristic of many stents in the market is longitudinal axis symmetry. Some of the stents, such as the Medtronic WIKTOR™ stents and the Medtronic InStent CARDIOCOIL™ stents, have a spiral structure. Such spiral structures have a cyclic helical coil element called "pitch." Other stents, such as the ACS MULTILINK™ stent, the Johnson & Johnson PALMAZ-SCHATZ™ stent, and the Medtronic Instent beSTENT™, are designed with a cyclic mesh element. Further stents such as the Johnson & Johnson Articulated Stent and the NIR stent have a double cyclic structure, that is, odd and even longitudinal elements where an odd element comes after an even element, and all the odd elements are identical and all the even elements are identical.

All the above stents have in common the characteristic of the uniformity of flexibility or durability for bending along the length of the stent.

Tests done on long stents loaded with bending stresses reveal a large bending moment in the central area of the stent. (See, for example, FIGS. 1a–1f.) Such stresses may cause fatigue-and even fracture at the center of the stent. On the one hand, significant stent flexibility is required during deployment while, on the other hand, significant rigidity is required in the expanded state of the stent. Since the bending moment increases from zero at the ends of the stent to a maximum value at the center, it has been determined that there is a need for a stent having a significant durability for bending at the exact place where the durability is required, that is, at the middle of the stent.

OBJECTS OF THE INVENTION

It is an object of this invention to provide a novel stent which does not have the disadvantages inherent in known stents.

It is also an object of this invention to provide a stent having variable flexibility and/or durability and/or stiffness.

It is further object of the invention to provide a stent having a large or significant durability for bending, i.e., rigidity or stiffness, at the middle portion of the stent.

These and other objects of the invention will become apparent to one skilled in the art from the discussion below.

SUMMARY OF THE INVENTION

The present invention provides for a novel stent which overcomes many of the disadvantages associated with various prior art stent designs which rely upon a stent construction which provides for a uniformly rigid construction or a uniform alternating rigid/less rigid construction. The invention provided for herein is directed to a stent having variable flexibility and moment along its length. The stent comprises portions of the stent having different bending and durability characteristics, as designed. In one embodiment of the invention, the members of the stent have components that have been designed to impart different load characteristics.

BRIEF DESCRIPTION OF THE DRAWINGS

FIG. 2 is an oblique view of one embodiment of the invention; and

DESCRIPTION OF THE PREFERRED EMBODIMENT

Figure 1A:
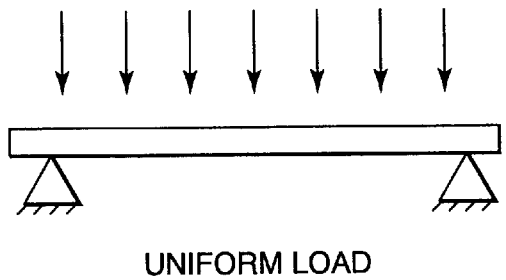
FIGS. 1a–1f are diagrams of loading studies of various stents.
Figure 1B:
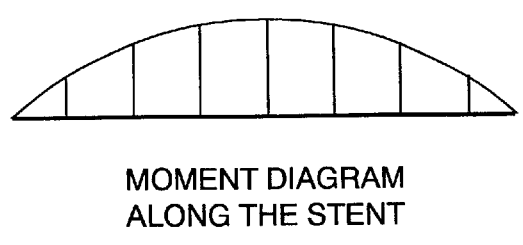
Figure 1C:
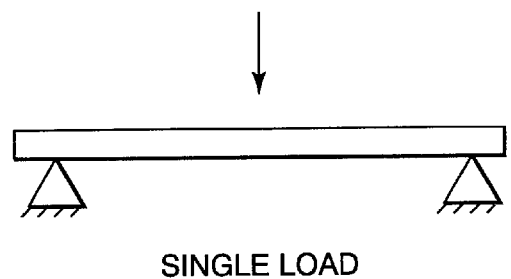
Figure 1D:
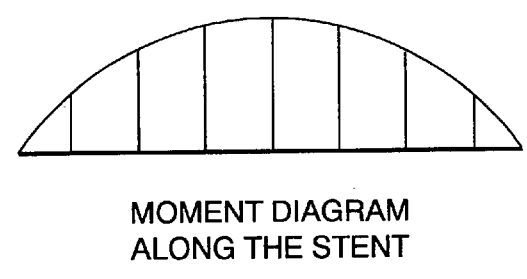
Figure 1E:
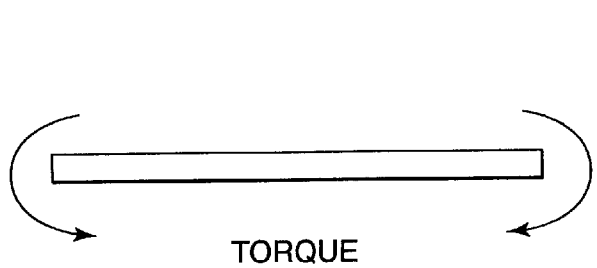
Figure 1F:
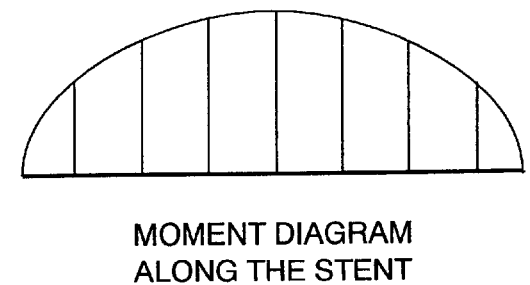

The invention can perhaps be better appreciated by making reference to the drawings. In FIG. 2, a stent 1 is positioned on the outer surface of a catheter 3. Stent 1 in this embodiment comprises a mesh lattice construction having sections 5, 7, 9, 11, 13, and 15 which are of varying degrees of flexibility or stiffness. For example, end sections 5 and 15 are comprised of smaller diameter and, therefore, less rigid mesh, inner sections 7 and 13, are comprised of larger diameter and more rigid mesh, and center sections 9 and 11 are comprised of even larger diameter and still more rigid mesh.

Annular cross members 19 are shown in FIG. 2 to be substantially similar in size, both in length and cross-section. However, it is within the scope of the invention that cross members 19 can vary in size, especially cross-section, and impart different rigidity to stent 1. Similar to the discussion above for sections 5, 7, 9, 11, 13, and 15, cross members 19 could have a larger cross-section near the middle of stent 1 and increasingly smaller cross-sections toward the ends of stent 1.

Figure 3:
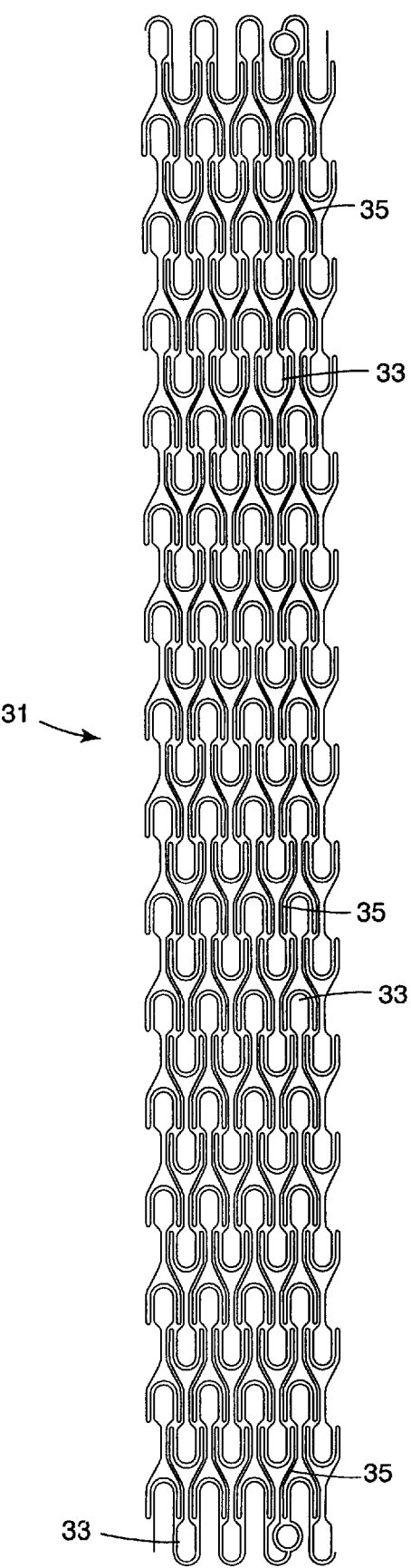
FIG. 3 is a plan view of another embodiment of the invention.

Another embodiment of the invention is represented in FIG. 3 by the partial lattice-work section 31 of a balloon-expandable stent where annular members 33 expand as a dilatation balloon is expanded within the stent. Cross members 35 will continue to "link" members as the stent expands. While annular member 33 can be of similar size and rigidity, according to the invention members 33 will differ in size, e.g., thickness or even length, over the length of stent 31, to provide desired characteristics. It is anticipated that, as described before for the embodiment of FIG. 2, cross members 35 will be more rigid toward the longitudinal center of stent 31 and less rigid toward the ends.

The actual dimensions of stents according to the invention will vary dependent upon intended use and the characteristics to be imparted. For example, for a stent intended for cardiovascular use and having an expanded length of from about 3 to 10 cm, the annular members and/or cross members may each have a cross-sectional profile of from about 0.01 to 0.10 cm, varying as discussed above.

The stents according to the invention can be comprised of a variety of materials known to be useful in fabricating stents, such as stainless steel, nitinol, tantalum, and/or other metals or alloys. If the stent is a mesh, the mesh can be formed, stamped, or etched to vary the size and/or diameter of the mesh components. Alternatively, the mesh could be formed from component members of different diameters that are soldered or welded together. Fabrication is discussed more below.

It is within the scope of the invention that a stent having variable stiffness could be comprised of other than a mesh. For example, a spiral coil stent could be formed from wire of variable diameter where the rigidity or stiffness of certain portions would vary according to the diameter. Preferably the end portions would be of a small diameter with gradual or step increases in diameter occurring toward the center of the stent.

A primary characteristic of stents according to the invention is that the moment diagrams, such as are shown in FIGS. 1a–1f, will be modified to avoid an unacceptable load, or peak, in the middle. Thus, in the stents according to the present invention the load will be distributed more evenly across the entire length of the stent.

The manufacture of stents according to the presentation invention may be accomplished via any of a variety of methods.

In one method of fabrication of a patterned etched cylinder a wire mesh is formed from a flat planar surface and then its two opposite edges are fused to create a cylinder. This method, however, suffers a basic disadvantage in that the presence of the fusing line creates a weakened area along the longitudinal axis of the stent, which is potentially subject to fatigue and breakage. Therefore, it is preferable for the stent to be formed from a more uniform piece of material to avoid this potential problem.

There are also two alternative methods for imaging the desired pattern, i.e, the location of points, undulating connectors, ring and connecting segments, etc., as may be required by a particular stent design onto a continuous cylinder, without the need of fusing into a cylinder after forming of the design. These methods, a film contact imaging method and a laser scanning method, are disclosed in co-pending U.S. patent application Ser. No. 08/543,337, filed Oct. 16, 1995, the teachings of which are incorporated herein by reference.

As has been described in more detail in said co-pending application, the film contact imaging method is carried out using an elliptical mirror which reflects ultraviolet light from an ultraviolet light source. The ultraviolet light source is located at one focal point of the elliptical mirror and illuminates through a slit of narrow aperture (which eliminates scattered light). The slit or aperture is located at the other focal point of the elliptical mirror to allow for high density power illumination from the ultraviolet source. Rays of ultraviolet light are thus reflected off of the elliptical mirror to pass through the slit or aperture and onto a moving film. The slit extends parallel to the longitudinal axis of a hollow tube or cylinder. The film carries the design sought to be provided onto the surface of the tube or cylinder.

The film is in contact with the hollow cylinder. The hollow cylinder is made of material which is to be fabricated into the stent of the present invention. The film serves as a mask or template, being transparent to ultraviolet light in some areas and opaque to ultraviolet light in others in the predefined stent pattern. The cylinder is coated with an appropriate material (a photoresist) for a photo-etching process. As ultraviolet light is transmitted onto the film through the slit, the film moves past the cylinder while the cylinder rotates. The rotation of the cylinder is correlated with the movement of the film to appropriately image the pattern on the film around and onto the cylinder. As a result, ultraviolet light passing through UV-transparent portions of the film template will strike the cylinder in the desired pattern to photoetch the appropriate configuration onto the cylinder. An acid treatment is then used to remove the areas which were struck by the UV light. In general, the chemical aspects of the system are similar to that used in the manufacturer of computer chips, i.e., photoresist, masking, acid, etc.

It should be pointed out that variations on this design will be understood by those of ordinary skill in the art. For example, in the presence of a sufficiently high powered light source, usage of an elliptical mirror is not essential.

The second, and preferred, method, which is also described in more detail in said co-pending application, uses a laser scanning system. The system consists of a cylinder or tube to be etched, a laser, the laser optics (containing beam components and modulator), and a dynamic deflector (such as a rotating mirror, a polygon, or any other known scanning deflector). The system is based upon a well-known flat bed scanning system. The cylinder is coated with a photoresist, or material suitable for photoetching. A laser is selected of the appropriate power and wavelength suitable for stimulating the photoresist in use. For example, for an ablation method, the laser can be high powered IR laser diode; for a photoresist sensitive to visible light, the laser can be a laser in the visible range or for a conventional UV photoresist, an Eximer laser or third (or higher) harmonic generation Nd:YAG/Nd:YLF laser can be used. The laser beam is shaped by an appropriate optical system, and modulated by direct modulation in the case of an IR laser diode, with AOM (an Acoustic optical Modulator) in the case of a CW laser in the visible, or by a vibrating mirror in the case of a UV laser.

The laser beam from the laser hits a deflector device which can be a rotating mirror, a polygon mirror, or other known scanning device. The beam emerges from the deflector, passing through a scan lens and is focused on the cylinder. The cylinder, which is coated with a photoresist, rotates about its longitudinal axis at a constant angular velocity, while the beam scans back and forth. The modulation of the laser beam allows writing a computer imaging file directly on the cylinder without the need of intermediate media (e.g. film). The laser scanning velocity is correlated to the cylinder angular velocity, and is determined by the energy required for exposure of the photoresist.

It is contemplated that the stents according to the present invention may also be fabricated by any of a variety of other methods and techniques available to the art without departing from the spirit or scope of the invention.

It is also contemplated that the stents of the present invention may be constructed in any of a number of configurations and arrangements known in the art so long as the primary requirement of the invention is met, that being that the stent be constructed in such a manner that the end product stent is provided with a varying degree of flexibility and stiffness along the length of the stent.

It will thus be seen that the objects set forth above, among those made apparent from the preceding description, are efficiently attained and, since certain changes may be made in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A stent comprising a plurality of expandable annular members; and a plurality of cross members having ends, the ends of each cross member being attached to an annular member at a point in common with a longitudinally adjacent cross member; the cross members differing in their relative rigidity and positioned so as to vary the bending flexibility of the stent along its length.

2. The stent of claim 1 comprising a plurality of dimensionally variable members.

3. The stent of claim 1 comprising a plurality of compositionally variable members.

4. The stent of claim 1, wherein the cross members positioned at the ends of the stent are less rigid than the cross members positioned at the center of the stent, such that the bending flexibility of the stent is greater at the ends of the stent than in the middle of the stent.

5. The stent of claim 1 fabricated from at least one material selected from the group consisting of stainless steel, nitinol, titanium, tantalum, and other metals and metal alloys.

6. The stent of claim 1, which has been fabricated using a method selected from the group consisting of forming, stamping, and etching.

7. The stent of claim 1, which has been fabricated using a film contact imaging method.

8. The stent of claim 1, which has been fabricated using a laser cutting method.

9. The stent of claim 1, wherein both the expandable annular members and the cross members differ in their relative rigidities.

10. The stent of claim 1 comprising a plurality of distal ends and a middle portion, wherein the bending flexibility of the stent is greater at the distal ends than at the middle portion.

* * * * *

UNITED STATES PATENT AND TRADEMARK OFFICE
CERTIFICATE OF CORRECTION

PATENT NO. : 6,287,336 B1  Page 1 of 1
DATED : September 11, 2001
INVENTOR(S) : Oren Globerman et al.

It is certified that error appears in the above-identified patent and that said Letters Patent is hereby corrected as shown below:

Title page,
Item [56], U.S. PATENT DOCUMENTS, please insert -- et al. -- after "Schwartz"; and please insert -- et al. -- after "Pinchasik".

Column 2,
Line 31, please delete "cross" occurring after "Annular".
Line 33, please delete "cross" occurring after "scope of the invention that" and insert -- annular -- therefor.
Line 36, please delete "cross" occurring after "sections 5, 7, 9, 11, 13, and 15," and insert -- annular -- therefor.

Signed and Sealed this

Twenty-sixth Day of November, 2002

*Attest:*

JAMES E. ROGAN
*Attesting Officer*     *Director of the United States Patent and Trademark Office*